United States Patent [19]

Rodebush

[11] 4,331,466
[45] May 25, 1982

[54] SELECTIVE RICE HERBICIDE
[75] Inventor: James E. Rodebush, Papillion, Nebr.
[73] Assignee: Stauffer Chemical Company, Westport, Conn.
[21] Appl. No.: 193,213
[22] Filed: Oct. 1, 1980
[51] Int. Cl.$^3$ ............................................ A01N 43/00
[52] U.S. Cl. ...................................... 71/88; 71/DIG. 1
[58] Field of Search ............................. 71/88, DIG. 1
[56] References Cited

U.S. PATENT DOCUMENTS

| | | | |
|---|---|---|---|
| 3,781,305 | 12/1973 | Teach | 71/88 |
| 3,834,892 | 9/1974 | Moon et al. | 71/DIG. 1 |
| 3,887,472 | 6/1975 | Kirby et al. | 71/88 |
| 4,035,178 | 7/1977 | Konz | 260/340.7 |
| 4,036,630 | 7/1977 | Toyama et al. | 71/18 |
| 4,042,369 | 8/1977 | Barker et al. | 71/88 |
| 4,155,915 | 5/1979 | Arndt et al. | 71/88 |
| 4,207,088 | 6/1980 | Konz | 260/340.7 |

*Primary Examiner*—Glennon H. Hollrah
*Attorney, Agent, or Firm*—Harry A. Pacini

[57] ABSTRACT

This invention relates to a herbicidal compound which demonstrates particular utility as a selective rice herbicide when applied postemergence postflood to paddy rice and to the method of use.

7 Claims, No Drawings

SELECTIVE RICE HERBICIDE

BACKGROUND OF THE INVENTION

This invention relates to a herbicide compound which demonstrates particular utility as a selective rice herbicide when applied post-emergence postflood to paddy rice; therefore this invention also relates to a novel herbicidal compostion for use in paddy rice fields.

DESCRIPTION OF THE PRIOR ART

Among existing herbicides used in transplanted paddy fields, pentachlorophenol, diphenyl ethers, etc., are well known for their excellent herbicidal effects when applied at the initial stage of growth of weeds. On the other hand, DCPA and SWEP.M (a mixture containing 20% of methyl-N-(3,4-dichlorophenyl) carbamate and 0.7% of ethyl 2-methyl-4-chlorophenoxy acetate) are also used as a herbicide but they are applied after the weeds have grown to some extent. DCPA, however, required drainage of water completely from the paddy fields before its application. If the draining is insufficient, DCPA fails to give satisfactory weeding effects. In this connection, it is practically extremely difficult to drain water completely from paddy fields, so that DCPA is rarely employed in practical application. SWEP.M may be used in fields filled with water, but its herbicidal effects and phytotoxicity on rice plants vary considerably depending on particular temperatures and soil conditions, i.e., the herbicidal activities of the agent are reduced under low temperature conditions while the adverse effects of the agent become pronounced under high temperature conditions. Furthermore, in the paddy field with continued leaching of water, the agent penetrates into the soil and is absorbed by roots of the rice plants, causing damage to the rice plants.

In addition, when SWEP.M is used in combination with carbamate or organic phosphorus base insecticides, a great problem occurs in practical applications in that rice plants are seriously damaged. Accordingly, it is strongly desired to develop a novel herbicide which has stable effects in removing weeds, which have grown to a certain degree, without resulting in phytotoxicity to the rice plants.

Other solutions to overcome the above-described disadvantages have been tried. For example, U.S. Pat. No. 4,036,630 relates to a herbicidal composition for use in paddy fields comprising α-(β-naphthoxy)-propionanilide and thiolcarbamate. However, such compositions require two active ingredients acting in concert. Ratios may vary and cause adverse effects if the ratio is not within that required to produce the desired effect for control of weeds with no injury to the rice crop.

SUMMARY OF THE INVENTION

It is therefore an object of the invention to provide a novel herbicidal composition which will overcome the above-described disadvantages.

It is another object of the invention to provide a herbicidal composition which is effective for controlling annual weeds or perennial weeds which have already grown to a certain degree in paddy rice fields.

It is still another object of the invention to provide a herbicidal composition which retains its herbicidal effects for a period of time.

It is yet another object of the invention to provide a herbicidal composition which may be used in paddy rice fields with selectivity to the rice under postemergence, postflood conditions.

An important feature of this invention resides in a herbicidal method and herbicidal composition for use in paddy rice fields comprising the compound 2-(m-methylureidophenyl)-5,5-diethyl-1,3-dioxane of the formula

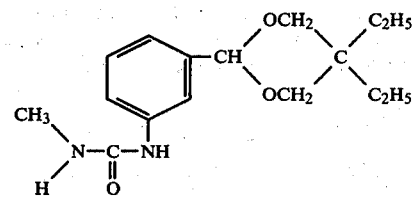

DESCRIPTION OF THE PREFERRED EMBODIMENT

The compound 2-(m-methylureidophenyl)-5,5-diethyl-1,3-dioxane (hereinafter referred to as MUPD for abbreviation) is described in U.S. Pat. No. 3,781,305, issued Dec. 25, 1973. The compound has a melting point of from 135° to 137° C.

The present invention relates to the discovery that the above-described compound as the active ingredient in an herbicidal composition has surprisingly remarkable effects for controlling weeds occurring in paddy rice fields and at the same time selectively no adverse herbicidal effect to paddy rice. Preferably, the compound is applied post-emergence postflood to paddy rice. The compound has the ability of controlling particularly annual weeds and perennial weeds in the postgrowth stage in the presence of paddy rice without injury to the rice.

The composition of the present invention includes MUPD which is effective for controlling annual and perennial weeds appearing and growing in flooded paddy rice fields. Moreover, the composition does not require drainage of the paddy fields and gives excellent effects when used in water-filled fields.

The compositions of the present invention are prepared using an inert carrier, inert diluent, inert filler or inert adjuvant, utilizing methods well-known to those skilled in the art of formulating, thereby making the compositions suitable for application as dusts, sprays, drenches, flowable formulations, wettable powders or granules in the form and manner required. The inert adjuvant is a stabilizing agent, a spreader, a penetrating agent or a wet spreader. Therefore the composition can be dispersed in water with the aid of such adjuvants or they can be employed in organic liquid composition such as emulsifiable concentrates, oil in water, water in oil emulsions, with or without the addition of secondary wetting, dispersing or emulsifying agents. Granular formulations can be made by extrusion or by spraying a solution of active ingredient on the solid substrate. An herbicidally effective amount depends upon the nature of the weed seeds or plants to be controlled and the rate of application can vary from about 1 to about 50 pounds per acre. The rate of application will be kept at a level safe for the paddy rice crops while exhibiting herbicidal effects on the weed species present in the paddy field.

SYNTHESIS OF 2-(M-METHYLUREIDOPHENYL)-5,5-DIETHYL-1,3-DIOXANE

Nine and four tenths grams (9.4 g) of 2-(m-aminophenyl)-5,5-diethyl-1,3-dioxane was reacted with 3 g of methyl isocyanate in 75 ml of acetone. The mixture was refluxed for between one and two hours and poured into water and the product collected by filtration. The yield was 11.7 g of the title compound, m.p. 112°–125° C. Trituration with diethyl ether raised the melting point to 135°–137° C.

EXPERIMENTAL EXAMPLE

Postemergence Postflood Evaluation for Rice Tolerance and Weed Control

Soil containers were filled to a depth of 2 inches with loamy sand soil pretreated with the fungicide CAPTAN®, and 18-18-18 fertilizer both at 50 ppm. Seeds of watergrass and rice were broadcasted one on either side of a row of curly dock which ran through the center of the soil container. The seeds were covered with 0.25 to 0.375 inch of soil. The soil was irrigated and kept moist until flooding. Eight days after planting the soil was flooded with 2.75 to 3 inches (7–8 cm) of water. One day later the candidate compound (treatment) was applied by pipetting a portion of a stock solution into the water or by sprinkling granules on the water surface. At the time of treatment the watergrass was 1 to 3.5 inches (3–9 cm) high, the rice was 1–2.75 inches (3–7 cm) high and the curly dock was in the cotyledon stage 0.75 inch (2 cm) high. Both the watergrass and rice were in the 2–3 true leaf stage.

The soil containers were located in a greenhouse with temperatures regulated for 65°–90° F. and the water level in the container were maintained at 2.75–3 inches (7–8 cm) in depth for the length of the test period.

In this test at 0.5 lb/Acre there was no (0 percent) injury to rice. The weed species curly dock and watergrass were injured and controlled 50 and 70 percent, respectively. Control standards were included for comparison.

Additional Test—Selective Rice Herbicidal Activity Postemergence Postflood Application

TABLE

| Rate lb/A | Percent Rice Injury | Percent Weed Control | | |
|---|---|---|---|---|
| | | Watergrass | Yellow nutsedge | Broadleaf weeds* |
| 0.25 | 0 | 42 | 0 | 46 |
| 0.5 | 0 | 68 | 2 | 74 |
| 2.0 | 12 | 94 | 1 | 100 |

*Average of:
annual morning glory
Sesbania
curly dock

It is apparent from the above results that the herbicidal composition of the present invention has useful selective weed-controlling effects. The herbicidal composition can easily be obtained as illustrated in detail in the following examples. All parts appearing in the examples are parts by weight.

EXAMPLE A 50 parts of MUPD, 45 parts of bentonite and 5 parts of sodium dodecylbenzenesulfonate were mixed to obtain 100 parts of a wettable powder.

EXAMPLE B 14 parts of MUPD, 83 parts of talc, 2 parts of polyoxyethylene glycol monolaurylate and 1 part of naphthalene sulfonate condensate were mixed together and then the resultant mixture was granulated by a conventional method using a granulating machine to obtain 100 parts of a granulate.

EXAMPLE C 12 parts of MUPD, 86 parts of talc and 2 parts of a polyethylene alkylphenyl ether were mixed together and the mixture was granulated by a conventional method using a granulating machine to obtain 100 parts of a granulate.

EXAMPLE D 50 parts of MUPD, 45 parts of talc and 5 parts of naphthalene sulfonate condensate were mixed to obtain 100 parts of a wettable powder.

EXAMPLE E 13 parts of MUPD, 40 parts of bentonite, 44 parts of talc, 2 parts of sodium ligninsulfonate and 1 part of polyoxyethylenesorbitanalkyl ester were mixed together and the mixture was granuled by a conventional method using a granulating machine to obtain 100 parts of a granulate.

EXAMPLE F 13 parts of MUPD, 84 parts of talc, 2 parts of sodium ligninsulfonate and 1 part of sodium dodecylbenzenesulfonate were mixed together and then the mixture was granulated by a conventional method using a granulating machine to obtain 100 parts of a granulate.

EXAMPLE G 40 parts of MUPD, 4 parts of a sodium alkylbenzenesulfonate and 56 parts of talc were mixed to obtain 100 parts of a wettable powder.

EXAMPLE H 14 parts of MUPD, 40 parts of bentonite, 43 parts of talc, 2 parts of sodium ligninsulfonate and 1 part of polyoxyethylene sorbitanalkyl ester were mixed together and the mixture was granuled by a conventional method using a granulating machine to obtain 100 parts of a granulate.

EXAMPLE I 14 parts of MUPD, 60 parts of bentonite, 2 parts of talc and 4 parts of sodium dodecylbenzenesulfonate were mixed together and the mixture was granulated by a conventional method using a granulating machine to obtain 100 parts of granulate.

EXAMPLE J 13 parts of MUPD, 60 parts of bentonite, 23 parts of talc and 4 parts of sodium N-methyl-N-oleoyl-laurate were mixed together and the mixture was granuled by a conventional method using a granulating machine to obtain 100 parts of granulate.

The phytotoxic compositions of this invention employing an herbicidally effective amount of the compound described herein are applied to the plants in the conventional manner. Thus, the dust and liquid compositions can be applied to the plant by the use of power-dusters, boom and hand sprayers and spray-dusters. The compositions can also be applied from airplanes as a dust or a spray because they are effective in very low dosages. In order to modify or control growth or germinating seeds or emerging seedlings, as a typical example, the dust and liquid compositions are applied to the flood water in a conventional method. It is not necessary that the phytotoxic compositions be admixed with the soil particles and these compositions can be applied merely by spraying or sprinkling the surface of the flood water. The phytotoxic compositions of this invention can also be applied by addition to irrigation water supplied to the field to be treated. This method of application permits the penetration of the compositions into the soil as the water is absorbed therein. Dust compositions, granular compositions, flowable concentrates, or liquid formulations applied to the surface of the water can be distributed to the weed plants therein. When the herbicide of the present invention is formed into granules, it is desired that such granules contain 1–20% by weight of the active composition of the present invention and when formed into a wettable powder, 10–50% active ingredient. When in the form of an emulsifiable concentrate, the composition is 5–35% active ingredient.

The phytotoxic compositions of this invention may also contain other additaments, for example, oil of various types, fungicides, nematocides, insecticides, bactericides, trace elements, fertilizers, antifoams (e.g., silicones), growth regulators, antidotes and other herbicidally effective amounts and the like, used as adjuvants or in combination with any of the above-described adjuvants. Other phytotoxic compounds useful in combination with the above described compounds include, for example, 2,4-dichlorophenoxyacetic acids, 2,4,5-trichlorophenoxyacetic acid, 2-methyl-4-chlorophenoxyacetic acid and the salts, esters and amides thereof; triazine derivatives, such as 2,4-bis(3-methoxypropylamino)-6-methylthio-S-triazine; 2-chloro-4-ethylamino-6-isopropylamino-S-triazine; and 2-ethylamino-4-isopropylamino-6-methylmercapto-S-triazine, urea derivatives, such as 3-(3,4-dichlorophenyl)-1,1-dimethylurea and 3-(p-chlorophenyl)-1,1-dimethylurea and acetamides such as N,N-diallyl-α-chloroacetamide, N-(α-chloroacetyl)-hexamethyleneimine, and N,N-diethyl-α-bromoacetamide, and the like; benzoic acids such as 3-amino-2,5-dichlorobenzoic; and thiocarbamates, such as S-propyl dipropylthiocarbamate; S-ethyl-dipropylthiocarbamate, S-ethylcyclohexylethylthiocarbamate, S-ethyl hexahydro-1H-azepine-1-carbothioate and the like. Fertilizers useful in combination with the active ingredients include, for example, ammonium nitrate, urea and superphosphate. Other useful additaments include materials in which plant organisms take root and grow, such as compost, manure, humus, sand the like.

The concentration of a compound of the present invention, constituting an effective amount in the best mode of administration in the utility disclosed, is readily determinable by those skilled in the art.

Various changes and modifications are possible without departing from the spirit and scope of the invention described herein and will be apparent to those skilled in the art to which it pertains. It is accordingly intended that the present invention shall only be limited by the scope of the claims.

What is claimed is:

1. The method of selectively controlling weed species occurring in paddy rice field cultures by applying postmergence postflood to said paddy field a rice selective but herbicidally effective amount of a compound having the formula.

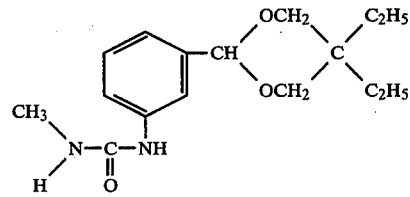

2. The method according to claim 1 wherein said compound is in the form of granules, a wettable powder, flowable formuations or an emulsifiable concentrate.

3. The method according to claim 2 wherein said granules contained therein from about 1 to about 20% of said compound.

4. The method according to claim 2 wherein said wettable powder contained therein from about 5 to about 50% of said compound.

5. The method according to claim 2 wherein said emulsifiable concentrate contained therein from about 5 to about 35% of said compound.

6. The method according to claim 1 wherein said compound is applied in an inert diluent, an inert filler or an inert adjuvant.

7. The method according to claim 6 wherein said inert adjuvant is a stabilizing agent, dispersing agent, suspending agent, spreader, penetrating agent or wet spreader.

* * * * *